United States Patent [19]
Sato et al.

[11] Patent Number: 5,470,081
[45] Date of Patent: Nov. 28, 1995

[54] CONTROL-SIGNAL INPUT DEVICE FOR COMPUTER GAME MACHINES

[75] Inventors: Toshiyuki Sato; George Sakamoto, both of Tokyo; Morikuni Takigawa, Kagoshima; Hirotoki Kawasaki, Tokyo, all of Japan

[73] Assignee: DFC Co. Ltd., Tokyo, Japan

[21] Appl. No.: 84,283

[22] Filed: Jun. 28, 1993

[30] Foreign Application Priority Data

Jun. 30, 1992 [JP] Japan .................................. 4-172393

[51] Int. Cl.⁶ ..................................................... A63F 9/24
[52] U.S. Cl. ........................ 273/438; 273/148 B; 273/460
[58] Field of Search ........................... 273/148 B, 148 R, 273/85 G, 433, 434, 435, 438, DIG. 28, 460

[56] References Cited

U.S. PATENT DOCUMENTS

| | | | |
|---|---|---|---|
| 4,149,716 | 4/1979 | Scudder | 273/85 G |
| 4,354,505 | 10/1982 | Shiga | 128/732 |
| 4,571,682 | 2/1986 | Silverman et al. | 364/413 |
| 5,213,338 | 5/1993 | Brotz | 273/460 |

FOREIGN PATENT DOCUMENTS

0177075  4/1986  European Pat. Off. ........... 273/148 B

OTHER PUBLICATIONS

Chin, Kathy, "Bio feedback replaces keyboards, joysticks", *Computers in Psychiatry, Psychology*, vol. 6(1), Winter 1984 p. 18.

*Primary Examiner*—Jessica J. Harrison
*Attorney, Agent, or Firm*—McGlew and Tuttle

[57] ABSTRACT

A control-signal input device for computer game machines for generating game control signals based on the analysis results of biological signals, such as brain waves, in which a biological signal extracted by a biological-signal extracting means is analyzed. Signal components of each of a plurality of frequency components in the biological signal are obtained based on the above analysis results. The state of the biological signal is obtained by subjecting the signal components of each of the frequency components to a predetermined processing. A predetermined game control signal is generated in accordance with the state of the biological signal, and transmitted to a game machine via a changeover device.

7 Claims, 5 Drawing Sheets ic # CONTROL-SIGNAL INPUT DEVICE FOR COMPUTER GAME MACHINES

BACKGROUND OF THE INVENTION AND RELATED ART STATEMENT

This invention relates generally to a control-signal input device for computer game machines, and more particularly to a control-signal input device for computer game machines using biological signals, such as brain waves, as game control signals.

Computer dame machines of conventional types, more specifically, typical computer game machines for one or more persons to play games on a TV screen comprise a game machine and a switch input section (hereinafter referred to as a joy pad). In this type of computer game machines, furthermore, game control signals (input signals) are usually generated as the player pushes the button on the joy pad.

As the player pushes the upper or lower arm of the cross-shaped button, a control signal for causing a game character image displayed on the TV screen to move in the vertical direction is produced. As the player pushes the right-hand or left-hand arm of the cross-shaped button, a control signal for causing the game character image to move in the horizontal direction is produced. Some joy pads incorporate separate A and B buttons, in addition to the cross-shaped button, to produce control signals to cause the character image to jump upward or to attack the enemy. In this way, a computer game is controlled as the player pushes the buttons on the joy pad to cause the character image on the TV screen to move, or manipulate it as he wishes.

In a computer game machine of the conventional type, a game proceeds as the player pushes the buttons of the joy pad, as described above. Consequently, the outcome of a game depends largely on the player's manual dexterity. With most game machines of the conventional types, the physically handicapped feel some difficulties in enjoying computer games. Furthermore, the progress or outcome of a computer game can hardly be affected by the degree of concentration of attention or excitement on the side of the player. As a result, in a simulation game that simulates a sport like golf, the outcome of which is dictated by psychological factors, the player cannot experience the feeling of actual golf play because the game machine does not reflect the state of mind of the player.

SUMMARY OF THE INVENTION

It is an object of this invention to provide a control-signal input device for computer game machines in which biological signals, such as brain waves, are analyzed, and game control signals are produced on the basis of the analysis results.

DETAILED DESCRIPTION OF THE EMBODIMENTS

Figure 1:
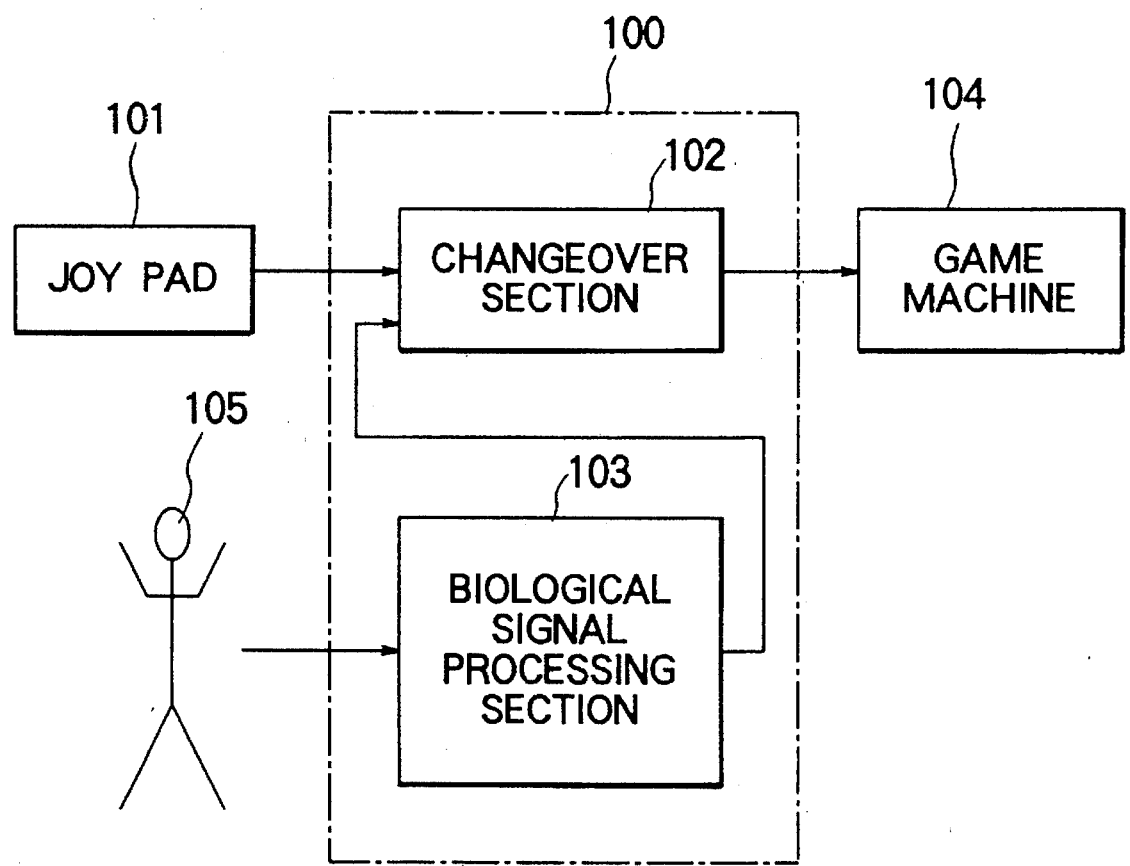
FIG. 1 is a block diagram illustrating the basic construction of this invention.

FIG. 1 is a block diagram illustrating the basic construction of this invention. In FIG. 1, reference numeral 100 refers to a control-signal input device incorporating a biological-signal processing section 103 and a changeover section 102. A signal detected on a player 105 by a sensor (not shown) is entered into the biological-signal processing section 103, and the game control signal output from the biological-signal processing section 103 is fed to a game machine 104 via the changeover section 102.

The biological-signal processing section 103 is a means to analyze a biological signal detected by a sensor, obtain signal components in each of a plurality of frequency components of the biological signal on the basis of the analysis results, obtain the state of the biological signal by subjecting the signal components of each of the frequency components to a predetermined processing, and produce a predetermined game control signal in accordance with the state of the biological signal.

The changeover section 102 is constructed so that signals (joy-pad signals) from the joy pad 101, which is a normal manual input means, can be input to the changeover section 102. The changeover section 102 is adapted to allow the joy-pad signal and the game control signal from the biological-signal processing section 103 to be fed to the game machine 104 by ORing or appropriately changing over these signals.

With the aforementioned construction, the game control signal is produced in the biological-signal processing section 103 based on the biological signal transmitted by the player 105. The game control signal thus produced is fed to the game machine 104 via the changeover section 102 to control the game. By doing this, the game can be played in accordance with the state of biological signals, such as brain waves, without the need for the player to push the buttons of the joy pad 101.

As a result, even a graying person whose motion nerves have been declining can win the game, or even a physically handicapped person can enjoy the game perfectly. Furthermore, the degree of concentration of attention by the player can be reflected in the outcome of the game. In the aforementioned golf game, for example, the game control signal is generated in such a manner that the directionality of the ball is stabilized (that is, the ball flies straight) when the degree of concentration of attention by the player is high (when a biological signal reflecting such a state is transmitted), or that the directionality of the ball becomes unstable (that is, the ball is sliced or hooked) when the degree of concentration of attention by the player is low (when the player is in excitement). As a result, the player can experience a feeling as if he (or she) is actually playing golf on a golf link.

An embodiment of this invention where the brain waves of a player is used as biological signals will be described in the following, using FIGS. 2 through 5.

In general, brain waves refer to changes in potential on the surface of the human brain (5–20 μV peak-to-peak) as expressed in frequency; the brain-wave range of 0.1–30 Hz being medically classified into four bands of δ (delta), θ (theta), α (alpha) and β (beta) rhythms.

Each of the brain-wave bands has the following meaning in terms of psychology.

(1) Delta rhythm: 0.5–3.5 Hz—associated with the state of sleep. It appears when a normal human adult is in the state of unconsciousness or deep sleep.

(2) Theta rhythm: 3.5–7.5 Hz—associated with doze or soft sleep. It appears when a human adult is relaxed or in the state of doze between sleep and consciousness.

(3) Alpha rhythm: 7.5–13.5 Hz—represents the concentrated state of the brain. It appears when a person is imaginative with the brain working efficiently.

(4) Beta rhythm: 13.5–30.5 Hz—encountered in a person who is in a state of tension. It appears when he reacts with information coming from the out side world, or leads his daily life full of apprehension, fear or excitement.

With the alpha rhythm as the basic parameter, the state where the alpha rhythm dominates more than 70% of the entire brain-wave spectrum is called the alpha rhythm-dominant state, the state where the alpha rhythm dominates 50–70% is called the alpha rhythm-semidominant state, the state where the alpha rhythm dominates 25–50% is called the mixed alpha rhythm state, and the state where the alpha rhythm dominates 0–25% is called the alpha rhythm-inferior state. The state of brain waves (biological signals) can be expressed by this classification.

Figure 2:
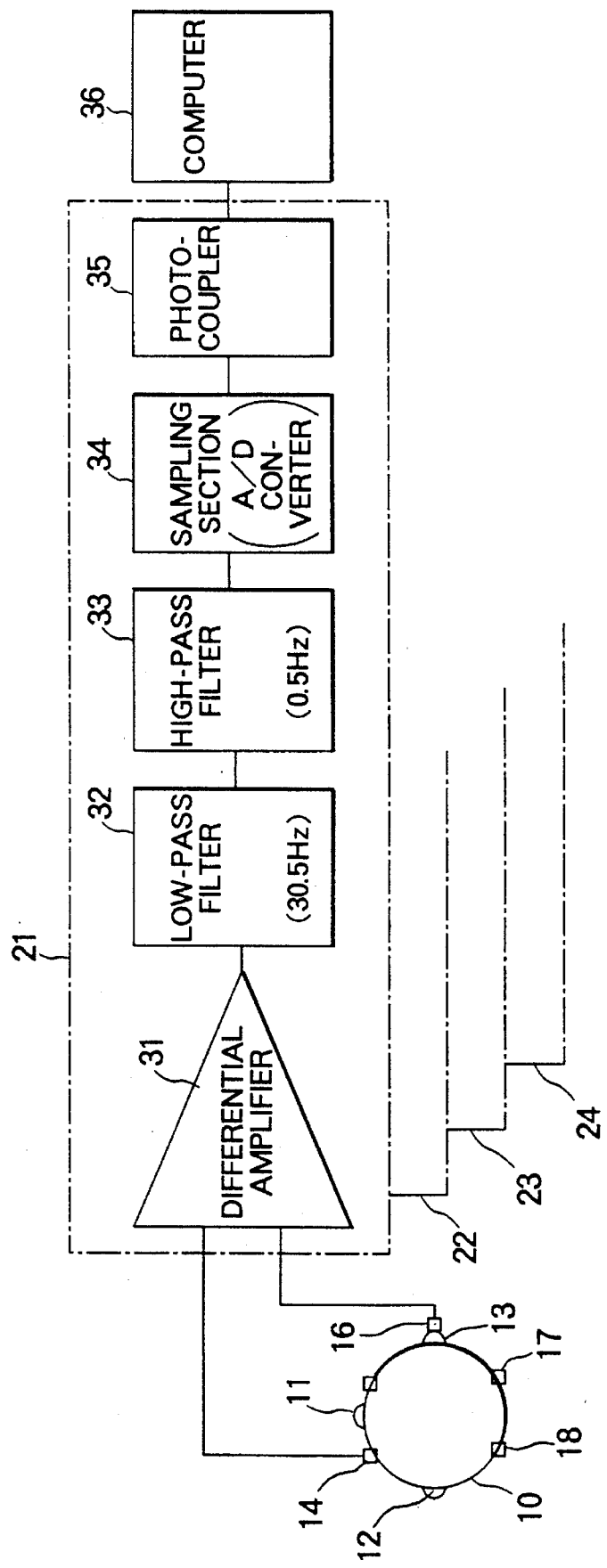
FIG. 2 is a block diagram illustrating an example of the construction of a biological-signal processing section in an embodiment of this invention.

FIG. 2 is a block diagram illustrating an example of the construction of the biological-signal processing section in an embodiment of this invention. In FIG. 2, numeral 10 refers to the brain of a player; 11 to his nose; 12 and 13 to his ears; 14–18 to sensors mounted on the head 10 to extract brain waves; 21–24 to units. In the units 21–24, a differential amplifier 31, a low-pass filter 32 (cutoff frequency: 30.5 Hz), a high-pass filter 33 (cutoff frequency: 0.5 Hz), a sampling section 34 and a photo-coupler 35 are connected in that order and incorporated. Signals from the photo-coupler 35 are input to the computer 36.

Connection is made so that the alternating signals from the sensors 14 and 16, on the other hand, are input to the differential amplifier 31 of the unit 21. Though not shown in the figure, connection is also effected so that the alternating signals from the sensor 16 are input as the reference signals to the differential amplifiers of the units 22–24, and that the alternating signals from the sensors 15, 17 and 18 are input to the differential amplifiers of the units 22–24. In this case, the number of sensors 14–18 to be mounted on the head 10 may be selected appropriately; the number of units for a player is determined in accordance with the number of sensors mounted on him (or her). Consequently, when a plurality of players play the game at a time, the required number of units 21–24 is the product of the number of sensors, as noted above, and the number of players.

In FIG. 2, the alternating signal extracted from the ear 13 by the sensor 16 is fed to the differential amplifier 31 of the unit 21, while the other alternating signal extracted from the head 10 by the sensor 14 is also fed to the differential amplifier 31; the resulting differential signal from the differential amplifier 31 is input to the low-pass filter 32 and the high-pass filter 33. Since signal components having frequencies exceeding 30.5 Hz are cut off in the low-pass filter 32, and those having frequencies less than 0.5 Hz are cut off in the high-pass filter 33, signal components in the frequency range of 0.5–30.5 Hz in the differential signal from the differential amplifier 31 are input to the sampling section 34.

The sampling section 34 samples and A/D converts the signals input in the aforementioned manner. The sampling results are fed to the computer 36 via the photo-coupler 35 to extract signal components of a plurality of frequency components (every 1-Hz width, for example).

In the other units 22–24, too, similar processing to the foregoing is performed.

With the aforementioned processing, brain waves can be analyzed to extract a predetermined frequency range, and thereby signal components for each frequency component can be obtained.

The patent application for means for obtaining signal components in each frequency component has already been filed (U.S. patent application 07/794,526).

Next, the computer 36 determines the state of brain waves through a predetermined processing to produce game control signals. That is, the computer 36 determines whether the brain wave at a given moment is in the alpha rhythm-dominant state (corresponding to the state of concentration), the beta rhythm-dominant state (corresponding to the state of excitation), or the theta rhythm-dominant state (corresponding to the state of relaxation). To this end, the state of brain wave is obtained by the following equation.

$$P = \frac{\int_{alpha} P(f) df}{\int_{all} P(f) df}$$

In this equation, the denominator is the total sum of the signal components in the entire frequency components (0.5 Hz–30.5 Hz), and the numerator is the total sum of the signal components in the alpha-rhythm band. In other words, P denotes the ratio of the integral of the alpha-wave signal components to the integral of the entire signal components. When $P \geq 0.70$, for example, the brain wave is of the alpha rhythm-dominant type.

By processing a brain wave with respect to beta and theta waves, whether the brain wave is of the beta rhythm-dominant type or of the theta rhythm-dominant type can be determined. It is assumed in this embodiment that delta rhythm may not be taken into account since it is associated with the state of sleep. Furthermore, predetermined control signals can be obtained by combining the states of signals; alpha rhythm, beta rhythm and theta rhythm.

By using the means for determining the dominant type of a brain wave based on the ratio of integrals, the dominant type for a brain wave is determined more accurately than with other conventional means relying on (the total sum of) the absolute amounts of signal components. Whereas reliance on absolute values tends to be affected by measuring conditions, leading to unstable results, the method relying on the ratio of integrals can avoid such inconveniences.

Furthermore, the following equation can be used instead of the aforementioned method using the ratio of integrals, $$Peak_{alpha} = max(P_{alpha}(f))$$

This equation means that the maximum value of the signal components for the frequency components (7.5 Hz–13.5 Hz) in the alpha-rhythm band is regarded as the peak (value) of the alpha rhythm. By subjecting beta and theta rhythms to similar processing to the foregoing, the peaks of the beta and theta rhythms can also be obtained.

Then, the ratio P' of the alpha-rhythm peak to the total sum of the entire peaks is obtained by the following equation.

$$P' = \alpha/(\alpha + \beta + \theta)$$

where α, β and θ are the peaks of the alpha, beta and theta rhythms. When $P' \geq 0.70$, for example, it can be said that the brain wave is of the alpha rhythm-dominant type. By subjecting the beta and theta rhythms to similar processing to the foregoing, whether the brain wave is of the beta rhythm-dominant type or the theta-dominant type can be determined.

By using the means for determining the dominant type of a brain wave with the ratio of peak values, the dominant type can be determined more accurately than with the aforementioned means relying on the ratio of integrals because the use of the ratio of integrals tends to be adversely affected by filter-bank properties, while the use of the ratio of peak values can eliminate such adverse effects.

Next, the computer 36 generates predetermined game control signals in accordance with the state of brain wave obtained in the foregoing.

Computer games played on the TV screen can be roughly divided into role-playing games, shooting games, action games, simulation games, etc.

Game control signals are generated using biological signals so that the following game control can be effected for each type of game.

(A) Control for role-playing game

When a request for selection is generated in this type of computer games, selection of one from among three alternative steps usually changes the development of the game, bringing the game closer to the end. In this invention, on the other hand, judgment is made as to whether the selection has been made after careful consideration, or haphazardly, on the basis of the degree of concentration of attention by the player at the time of selection, and the subsequent development of the game is changed, and game parameters or properties, such as treasures and weapons, are changed in accordance with the degree of concentration of attention by the player even when a right judgment has been made,
(1) State of concentration (alpha rhythm-dominant)
  The rate of improvement in the strength of the player is increased (accelerated).
  The power of weapons is changed accordingly.
  The frequency of suggestions on the locations of treasures is increased.
(2) State of excitement (beta rhythm-dominant)
  Strong enemies appear.
  The weapon in hand becomes weaker.
(3) State of relaxation (theta rhythm-dominant)
  The player in a relaxed state is readily beaten by the enemy.

(B) Control for shooting game (1) State of concentration (alpha rhythm-dominant)
  A shot or a spate of shots are discharged from the player's own plane.
  The power of weapons is improved.
  A shield wall is provided.
  The enemy becomes weaker.
(2) State of excitement (beta rhythm-dominant)
  No shots are discharged from the player's own plane.
  The power of weapons is lowered.
  The shield wall disappears.
  The enemy becomes stronger.
  Steady aim cannot be taken.
(3) State of relaxation (theta rhythm-dominant)
  The development of the entire game becomes slower.
  Allies increase in number.

(C) Control for action game

Among various computer games, action games are most widely played. Those which can scroll the screen is more popular than those having the static screen.
(1) State of concentration (alpha rhythm-dominant)
  The player himself becomes powerful as his ability to jump and attack is increased and his movement becomes more agile.
  The number of enemies becomes fewer.
(2) State of excitement (beta rhythm-dominant)
  The number of enemies and their offensive power are increased.
  The offensive power and other factors of the player are reduced.
(3) State of relaxation (theta rhythm-dominant)
  Although the motion of the player becomes slow, he can take more accurate aim.

(D) Control for simulation game

Most simulation games simulate sports, car racing, etc. In a conventional type of golf game as one of such simulation games, the development of the game changes according to the timing at which the player pushes the switch to hit the golf ball on the screen. In this invention, on the other hand, a control signal which corresponds to the degree of concentration by the player is input so that control can be effected to change the flight or behavior of the golf ball in accordance with the degree of concentration by the player.
(1) State of concentration (alpha rhythm-dominant)
  The directionality of the ball is stabilized (the ball flies straight).
  The flight of the ball is increased to the maximum possible flight for the club used.
  The flight of the ball differs in accordance with the degree of the alpha rhythm.
(2) State of excitement (beta rhythm-dominant)
  The directionality of the ball becomes unstable; the ball may be sliced or hooked.
  The flight of the ball is short; the ball may be topped or duffed, depending on the degree of excitement.

This invention can be applied not only to golf simulation games but also to tennis and baseball simulation games, offering players a feeling similar to that experienced in actual playing.

The computer 36 generates game control signals to effect the aforementioned control in accordance with the state of brain waves, and feeds them to the game machine 104 as an output to the biological-signal processing section 103 as shown in FIG. 1.

The computer 36 constituting the biological-signal processing section 103 may be provided on the side of the biological-signal processing section 103 or in the game machine 104 in FIG. 1. In the former case, the changeover section 102 is provided between the computer 36 and the game machine 104. In the latter case, the changeover section 102 is provided between the photo-coupler 35 and the computer 36.

The changeover section 102 is provided for the following reason. In the conventional game machines, joy-pad signals are fed in the form of parallel or serial signals to the game machine 104, and the joy-pad signals (as control signals) changes the development of the games as the computer of the game machine 104 reads them every 17 ms or so. In the conventional game machines, the number of signal lines is as small as only 8 to 15, limiting the amount of data to be input at one time.

8–15 signal lines are insufficient for transmitting up to 1030 control signals necessary for this invention. To cope with this, this invention eyes at the fact that the upper and lower arms of the cross-shaped,button of any joy pad used for game machines can never been mechanically turned ON simultaneously. That is, both the signal lines for transmitting command signals for upward and downward movement are turned ON simultaneously, while brain wave-based control signals are transmitted on the other signal lines (for example, signal lines for transmitting command signals for leftward and rightward movement by the A and B buttons, or the cross-shaped button). With this arrangement, data can be transmitted without changing hardware by causing game software to judge that data on the other signal lines are brain wave-based control signals through the simultaneous turning-ON of the command signals that could never occur in normal operations. This arrangement makes it possible to maintain interchangeability among multiple commercially available computer game machines.

Figure 3:
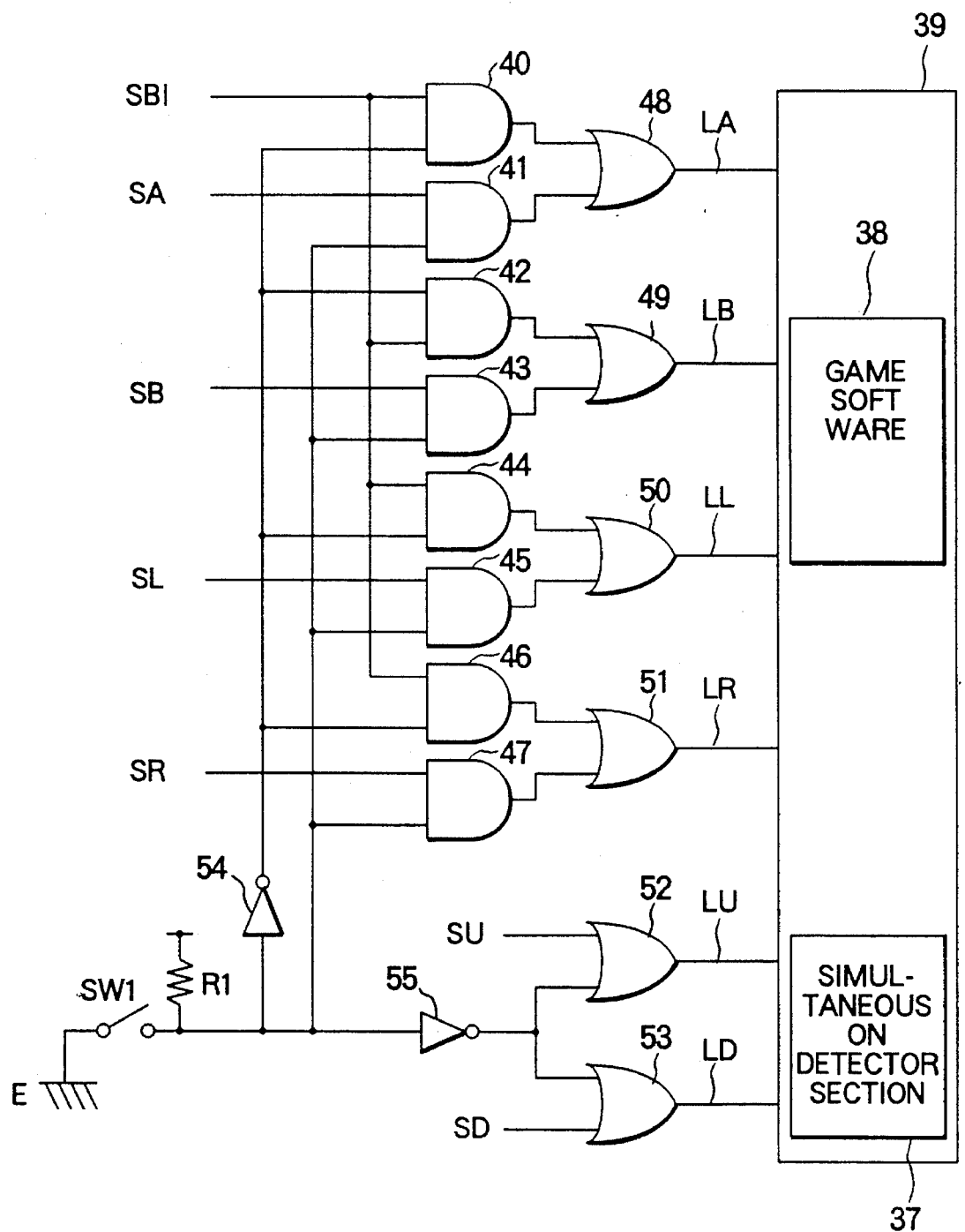
FIG. 3 is a diagram illustrating an example of the construction of the changeover section in FIG. 1.

FIG. 3 is a diagram of assistance in explaining the construction of the changeover section 102 shown in FIG. 1. In FIG. 3, numerals 40 through 47 refer to AND gates provided in parallel so that a biological signal and/or a signal from the joy pad can be input to any one of the terminals thereof. That is, the AND gates 40 through 47 are constructed so that the biological signal SBI can be input to any one of the terminals of the AND gates 40, 42, 44 and 46, and the joy-pad signals SA, SB, SL and SR can be input to any one of the terminals of the AND gates 41, 43, 45 and 47, respectively.

Furthermore, the AND gates 40 through 47 are constructed so that the output from a power source (not shown) is input to the other of the terminals of the AND gates 40, 42, 44 and 46 via a resistor R1 and a NOT gate 54, and that the output from the resistor R1 is input to the other of the terminals of the AND gates 41, 43, 45 and 47.

Numerals 48 through 51 refer to OR gates constructed so that the outputs from the AND gates 40 and 41, the outputs from the AND gates 42 and 43, the outputs from the AND gates 44 and 45, and the outputs from the AND gates 46 and 47 are input to the OR gates 48, 49, 50 and 51, respectively. The outputs from the OR gates 48 through 51 are fed to the computer 39 of the game machine via signal lines LA, LB, LL and LR.

Numerals 52 and 53 refer to OR gates constructed so that signals SU and SD from the joy pad can be input to any one of the terminals thereof, and that the output from the resistor R1 can be input via a NOT gate 55 to the other of the terminals thereof. SW1 denotes a switch connected in series between the resistor R1 and the earth E. LU and LD denote signal lines for transmitting joy-pad signals SU and SD, constructed so that the outputs from the OR gates 52 and 53 are fed to the computer 39, and that signals are fed to a simultaneous-ON detector section 37 provided in the computer 39. Numeral 38 refers to game software installed in the computer 39.

The operation of the embodiment having the aforementioned construction will be described in the following. In FIG. 8, even when the biological signal SBI is input to any one of the terminals of the AND gates 40, 42, 44 and 46 in a state where the switch SW1 is turned OFF, there are no outputs from the AND gates 40, 42, 44 and 46 since the other of the terminals (the terminals on the side of the NOT gate 54) of these AND gates are at the LOW level.

On the other hand, since the terminals of the AND gates 41, 43, 45 and 47 on the side of the resistor R1 are at the HIGH level, as the joy-pad signals SA, SB, SL and SR are input, they are output from the OR gates 48 through 51. Furthermore, as the terminals of the OR gates 52 and 53 on the side of the NOT gate 55 are at the LOW level, the OR gates 52 and 53 are in a state where they can receive the joy-pad signal SU or SD. Thus, when the respective signals are fed, outputs appear on the OR gates 52 and 53. No outputs, however, appear simultaneously on the OR gates 52 and 53. Consequently, the joy-pad signals SA, SB, SL, SR, SU and SD are fed to the OR gates 48 through 53, and to the computer 39 via the signal lines LA, LB, LL, LB, LU and LD, 20 permitting the player to play a game provided by the game software 38.

If the switch SW1 is turned ON by any appropriate means, as the player pushing the switch, for example, the power circuit, including the resistor R1, is shortcircuited, bringing the output side of the NOT gates 54 and 55 to a HIGH level, the AND gates 40, 42, 44 and 46 are made ready to be opened if the inputs on the other side are changed to a HIGH level, and the AND gates 41, 43, 45 and 47 are closed. At the same time, the or gates 52 and 53 are turned ON simultaneously, and the simultaneous-ON detector section 37 incorporated in the computer 39 detects this state, and notifies the game software 38 of the fact that the switch SW1 has been turned ON. With this, the biological signal SBI is fed from the four AND gates 40, 42, 44 and 46 to the four signal lines LA. LB, LL and LR via the corresponding four OR gates 48 through 51. Thus, the game software 38 comes to recognize that the biological signal SBI has been transmitted.

The game software 38 works in such a manner as to fetch the signals on the signal lines LA, LB, LL and LR at a predetermined interval (every 17 ms, for example). At this moment, the game software 38 learns from the notice given by the simultaneous-ON detector section 37, as described above, that the signals on the signal lines LA, LB, LL and LR are biological signals, performs a predetermined processing to generate control signals that act in place of game control signals corresponding to the fetched biological signals.

In this case, there can be the following three types of patterns in which the game is controlled by the control signals from the computer 39.

(1) 1st pattern

In the case where the biological signal SBI is one type of d-c signal involving only ON and OFF, with the alpha rhythm accounting for 50% of the entire biological signal SBI as the standard, for example, when the biological signal SBI is fed to the signal lines LA, LB, LL and LR in the aforementioned manner within a predetermined time after the switch SW1 is turned ON in FIG. 3, the computer 39 detects the biological signal SBI on any one of the above-mentioned four signal lines to produce a control signal to change or switch over the screen modes; i.e., "The motion of the game character image becomes slow," or "The number of enemies confronting the game character decreases," for example, on the TV screen.

(2) 2nd pattern

In this pattern, the biological signals SBI are multiple types of alternating signals the specific types of which can be distinguished by the state of modulation, for example. In this case, as any of the multiple types of the biological signals SBI is fed within a predetermined time after the switch SW1 shown in FIG. 3 is turned ON, the computer 39 detects the biological signal SBI on any of the four signal lines LA, LB, LL and LR, identifies the type thereof, and produces a control signal that selects from among a plurality of game software programs one mode relevant to that biological-signal type. To achieve this, the computer 39 must have a function to identify the type of the biological signal SBI, though not shown in the figure.

(3) 3rd pattern

In this pattern, there are four types of signals as the biological signals SBI which are different in accordance with the state of modulation and correspond with the joy-pad signals SA, SB, SL and SR, respectively. In this case, after the switch SW1 shown in FIG. 3 is turned ON, the computer 39 produces a control signal to perform operations corresponding to the joy-pad signal SA for the biological signal SBI input from the signal line LA, for example. Similarly, the computer 39 produces control signals to perform operations corresponding to the joy-pad signals SB, SL and SR, respectively, for the biological signals input from the other signal lines LB, LL and LR. In this case, too, the computer 39 must have a function to identify the type of the biological signal SBI.

Figure 4:
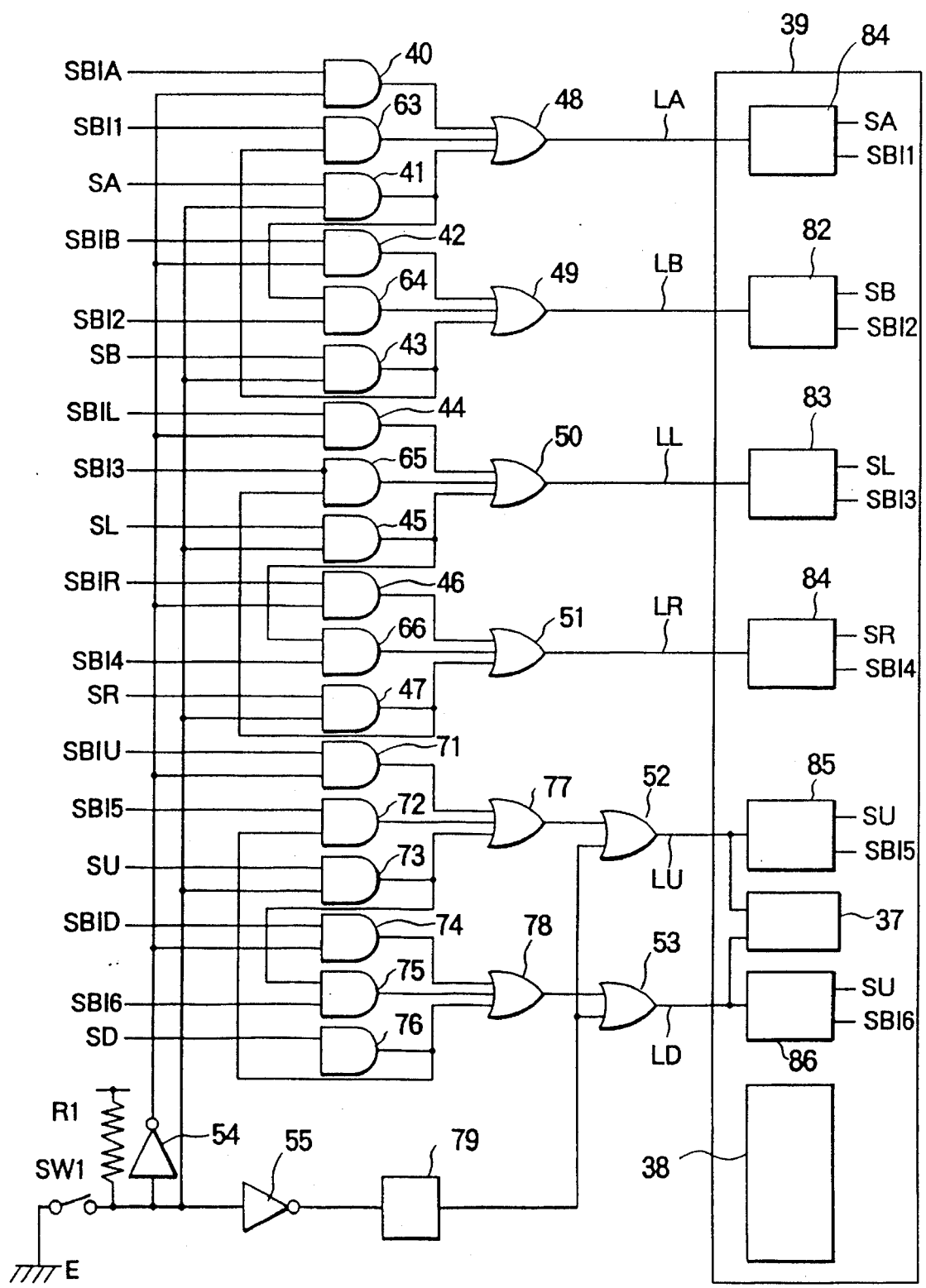
FIG. 4 is a diagram illustrating another example of the construction of the changeover section in FIG. 1.
Figure 5:
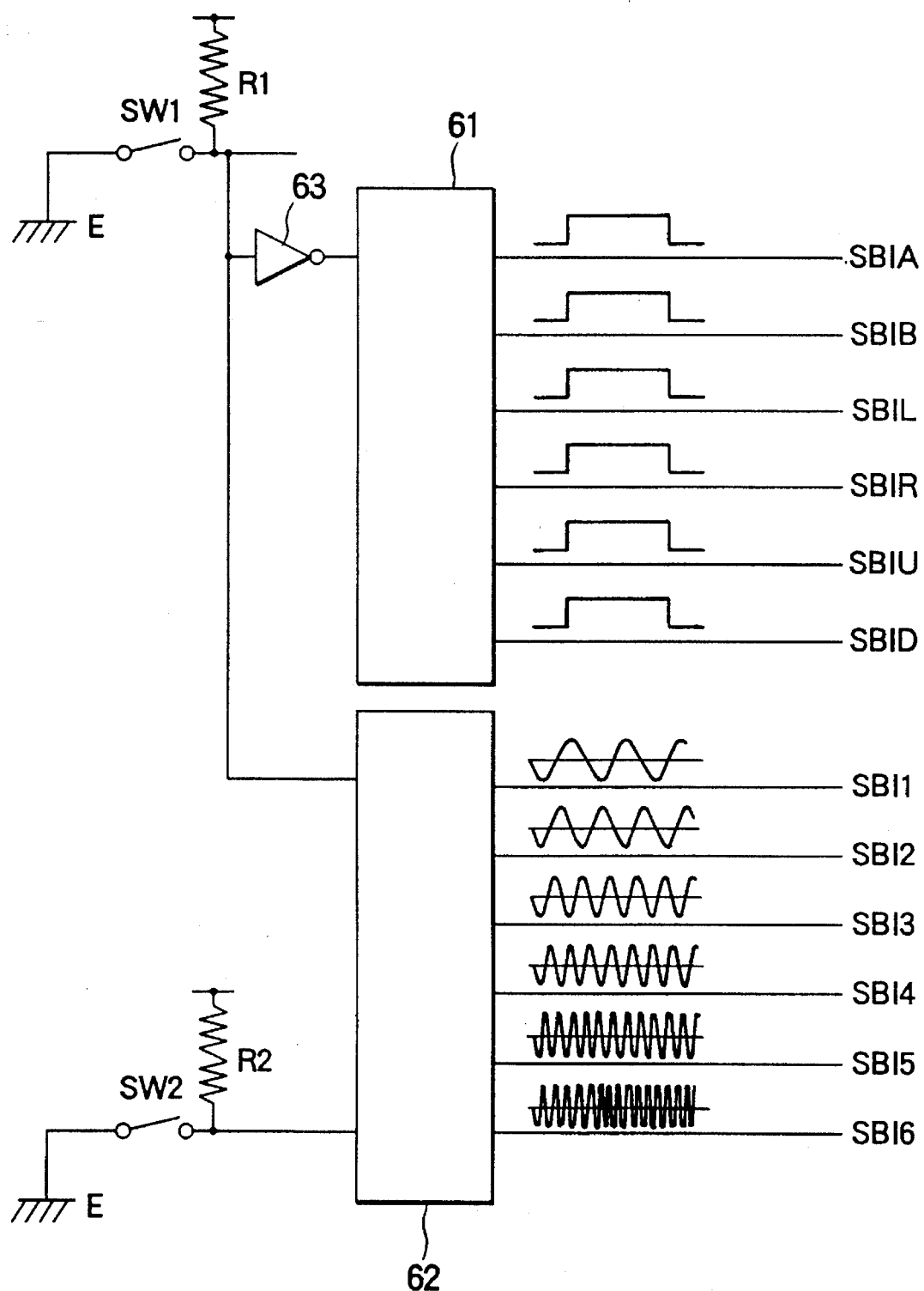
FIG. 5 is a diagram illustrating an example of a biological-signal waveform shaping section for transmitting biological signals to the changeover section in FIG. 4.

FIG. 4 is a diagram of assistance in explaining another construction of the changeover section shown in FIG. 1. FIG. 5 is a diagram of assistance in explaining an example of the biological-signal waveform shaping section for transmitting biological signals to the changeover section shown in FIG. 4. Like parts are indicated by like numerals used in FIG. 3. FIG. 5 will be described in the following, prior to FIG. 4. In FIG. 5, numerals 61 and 62 are first and second biological-signal waveform shaping sections, which output six types of SBIA, SBIB, SBIL, SBIR, SBIU and SBID, and six types of biological signals SBI1 through SBI6, respectively. The former group of biological signals SBIA through SBID are d-c signals, which are identical to the joy-pad signals SA, SB, SL, SR, SU and SD shown in FIG. 3. The latter group of biological signals SBI1 through SB6, on the other hand, are a-c signals selected appropriately in accordance with the contents of the game.

In the first biological-signal waveform shaping section 61, the output from a power source (not shown) is input via the resistor R1 and a NOT gate 63, while the output from the resistor R1 is input directly to the second biological-signal wave-form shaping section 62. In the second biological-signal waveform shaping section 62, the output from the power source (not shown) is also input via a resistor R2. A switch SW2, when pushed, inhibits the operation of the second biological-signal waveform shaping section 62.

In FIG. 4, numerals 63 through 66 refer to AND gates to which the biological signals SBI1 through SBI4 are input, and which output signals to the OR gates 48 through 51. The AND gates 63 through 66 are constructed so that the output from the AND gate 41, to which the joy-pad signal SA is input, is also input to the AND gate 64, to which the biological signal SBI2 is input, and so that the output from the AND gate 43, to which the joy-pad signal SB is input, is also input to the AND gate 63, to which the biological signal SBI1 is input. Similarly, the AND gates 63 through 66 are constructed so that the output from the AND gate 45, to which the joy-pad signal SL is input, is also input to the AND gate 66, to which the biological signal SBI4 is input, and so that the output from the AND gate 47, to which the joy-pad signal SR is input, is also input to the AND gate 65, to which the biological signal SBI3 is input.

Next, numerals 71 through 76 refer to AND gates disposed in the same manner as described above. That is, the AND gates 71 through 76 are constructed so that the output from a power source (not shown) is input to any one of the terminals of the AND gates 71 and 74 via the resistor R1 and the NOT gate 54, and so that the output from the resistor R1 is input to any one of the terminal of the AND gate 73. The biological signals SBIU and SBI5, the joy-pad signal SU, the biological signals SBID and SBI6, and the joy-pad signal SD are input to the AND gates 71 through 76,, respectively. The outputs from the AND gates 76 and 73 are input to the AND gates 72 and 75.

The outputs from the AND gates 71 through 73 are output to the OR gate 77, and the outputs from the AND gates 74 through 76 to the OR gate 78, respectively. The outputs from the OR gates 77 and 78 are output to the OR gates 52 and 53. To the other of the terminals of the OR gates 52 and 53, the output from the resistor R1 is input via the NOT gate 55 and a one-shot multi-vibrator 79. Next, numerals 81 and 86 refer to DC/AC judgment circuits incorporated in the computer 39, connected to the signal lines LA, LB, LL, LR, LU and LD, respectively, to judge whether signals on these signal lines are d-c signals or a-c signals.

The operation of the aforementioned construction will be described in the following, referring to FIGS. 4 and 5. In order to input only the joy-pad signals SA, SB, SL, SR, SU and SD shown in FIG. 4 using the joy pad 101 shown in FIG. 1, the switch SW1 is turned OFF and the switch SW2 is turned ON. This causes the AND gates 40, 42, 44, 46, 71 and 74 shown in FIG. 4 to be closed, bringing the first and second biological-signal waveform shaping sections 61 and 62 into an inoperative state. Thus, only the joy-pad signals SA, SB, SL, SR, SU and SD are fed to the signal lines LA, LB, LL, LR, LU and LD in FIG. 4, while d-c signals SA, SB, SL, SR, SU and SD are transmitted as control signals from the computer 39 to cause the game to proceed.

In order to transmit only the biological signals SBIA, SBIB, SBIL, SBIR, SBIU and SBID, both the switch SW1 and the switch SW2 are turned ON. This causes only the AND gates 40, 42, 44, 46, 71 and 76 shown in FIG. 4 to be ready to be turned ON, and the remaining AND gates are closed. As the output from the NOT gate 55 changes to a HIGH level, the simultaneous-ON detector section 37 is actuated by the output from the one-shot multivibrator 79 via the OR gates 52 and 53 and the signal lines LU and LD to notify the game software of the results.

Thus, the six types of the biological signals (d-c signals) SBIA, SBIB, SBIL, SBIR, SBIU and SBID corresponding to the six types of the joy-pad signals SA, SB, At, SR, SU and SD are transmitted from the first biological-signal waveform shaping section 61 to the signal lines LA, LB, LL, LR, LU and LD via the opened AND gates 40, 42, 44, 46, 71 and 74 and the OR gates 48 through 51, 77, 78, 52 and 53. Consequently, these signals are judged as d-c signals by the DC/AC judgement circuits 81 through 86 incorporated in the computer 39, and the joy-pad signals SA, SB, SL, SR, SU and SD, which are d-c signals, are transmitted as control signals, to cause the game to proceed, as in the case of the aforementioned transmission of joy-pad signals only.

Next, the simultaneous transmission of joy-pad signals and biological signals will be described. In this case, the switches SW1 and SW2 are turned OFF. As a result, the first biological-signal waveform shaping section 61 shown in FIG. 5 is not in an operative state, and the second biological-signal waveform shaping section 62 is brought into an operative state, shaping the waveforms of the six types of the biological signals SBI1 through SBI6. These biological signals SBI1 through SBI6 are modulated a-c signals, as shown in FIG. 5. The AND gates 40, 42, 44, 46, 72 and 75 shown in FIG. 4, on the other hand, are all closed, so the biological signals SBIA, SBIB, SBIL, SBIR, SBIU and SBID, which are d-c signals, are not input. Since the AND gates other than those mentioned above are ready to be turned ON, the joy-pad signals SA, SB, SL, SR, SU and SD, which are d-c signals, and the biological signals SBI1 through SBI6, which are a-c signals, can be input in parallel. In this case, the computer 39 incorporating the DC/AC judgement circuits 81 through 86 can judge whether even those signals transmitted from the same signal lines are joy-pad signals or biological signals, and transmits them to the game machine as different control signals.

Since the computer 39 has a signal identifying function, as described above, there is no need, in the case of FIG. 5, to completely change over from the joy-pad signals to the biological signals; while one of the joy-pad signal is being transmitted, the biological signals may be transmitted using other empty (unused) signal lines. That is, since combinations of the signal lines LA and LB, LL and LR, and LU and LD are never used simultaneously in terms of the function of the joy pad, biological signals are transmitted using empty (unused) signal lines among them.

By providing the aforementioned construction, the control-signal input device for computer game machines not only maintains interchangeability with other game software programs but also can use control signals based on both joy-pad signals and biological signals. In a golf game, for example, "hitting the ball" can be input from the joy pad 101, while the directionality and other parameters of the ball can be determined in accordance with biological signals.

Although a preferred embodiment of this invention has been described in the foregoing, obviously many modifications and variations of this invention are possible in accordance with the spirit of the invention.

Although the ratio of integrals, etc. for determining the state of brain waves is assumed to be 70% in the embodiment, this value may be changed appropriately (in accordance with the contents of the game). Furthermore, the state of brain waves can be obtained by other means than the ratio of integrals, etc. For example, the zone in which the maximum integral value is obtained by integrating frequency components in each zone of the alpha rhythm may be assumed to the alpha rhythm-dominant zone, or the zone to which the maximum value of the frequency components belongs may be assumed to be the alpha rhythm-dominant zone.

Computer game machines may be those which can be used for fortune-telling or diagnosis of marital congeniality, aside from those used for the so-called games, and they are not limited to those relying on the TV (cathode-ray tube) screen, but may be those relying on the liquid-crystal screen.

Biological signals may be those detected by sensors from pulsation (and the coefficient of its variation) or changes in skin resistance due to perspiration, in addition to brain waves, and these may be used singly or in combination with other biological signals to produce control signals.

As described above, this invention makes it possible to produce game control signals based on biological signals, and to input them to the computer game machine so that the game can be played regardless of the manual dexterity of players.

What is claimed is:

1. A control-signal input device for computer game machines for inputting control signals to a computer game machine constructed so that peculiar operations are performed in accordance with a plurality of game control signals, comprising means for extracting biological signals, means for obtaining signal components of each of a plurality of frequency components in said extracted biological signals, and obtaining the state of said biological signals by performing a predetermined computational processing for said signal components, and means for supplying control signals that substitute for said game control signals in accordance with the state of said obtained biological signals;

said biological signals are brain waves, and the state of biological signals is obtained based on the ratio of the intensity of alpha-rhythm signal components, beta-rhythm signal components, or theta-rhythm signal components to the intensity of the entire signal components of each of a plurality of obtained frequency components.

2. A control-signal input device for computer game machines as set forth in claim 1 wherein said biological-signal extracting means comprises a low-pass filter and a high-pass filter so that computational processing is performed by extracting biological signals whose frequencies are lower than the cut-off frequency of said low-pass filter and higher than the cut-off frequency of said high-pass filter.

3. A control-signal input device for computer game machines as set forth in claim 1 wherein the ratio of the intensity of alpha-rhythm signal components, beta-rhythm signal components, or theta-rhythm signal components is obtained in the form of the ratio of the integral of alpha-wave signal components to the integral of the entire signal components.

4. A control-signal input device for computer game machines as set forth in claim 1 wherein the ratio of the intensity of alpha-rhythm signal components, beta-rhythm signal components, or them-rhythm signal components is obtained in the form of the ratio of the peak values of alpha rhythm, beta rhythm or theta rhythm to the total sum of the peak values of alpha rhythm, beta rhythm or theta rhythm.

5. A control-signal input device for computer game machines as set forth in claim 1 wherein said plurality of game control signals include switching-means output signals, said switching-means output signals being generated by manually operating a switching element.

6. A control-signal input device for computer game machines as set forth in claim 5 wherein said switching-means output signals and said control signals are input to said computer game machine under a selectively switchable mode.

7. A control-signal input device for computer game machines as set forth in claim 5 wherein said switching-means output signals and said control signals are input in parallel to said computer game machine.

* * * * *

UNITED STATES PATENT AND TRADEMARK OFFICE
CERTIFICATE OF CORRECTION

PATENT NO. : 5,470,081
DATED : November 28, 1995
INVENTOR(S) : SATO et al.

It is certified that error appears in the above-indentified patent and that said Letters Patent is hereby corrected as shown below:

On the title page: Item

[75] Inventor: Morikuni Takigawa, Kagoshima-ken, Japan
 Item
[73] Assignees: DFC Co.,Ltd., George Sakamoto, Hirotoki Kawasaki, all of Tokyo, Morikuni Takigawa, Kagoshima-ken, all of Japan Signed and Sealed this Fifth Day of March, 1996

Attest:

BRUCE LEHMAN

Attesting Officer  Commissioner of Patents and Trademarks